United States Patent
Gu et al.

(10) Patent No.: US 8,902,164 B2
(45) Date of Patent: *Dec. 2, 2014

(54) OPTICAL FINGER MOUSE, MOUSE CONTROL MODULE AND PHYSIOLOGY DETECTION METHOD THEREOF

(75) Inventors: Ren Hau Gu, Hsin-Chu (TW); Ming Tsan Kao, Hsin-Chu (TW); Sen Huang Huang, Hsin-Chu (TW)

(73) Assignee: Pixart Imaging Inc., Hsin-Chu (TW)

( * ) Notice: Subject to any disclaimer, the term of this patent is extended or adjusted under 35 U.S.C. 154(b) by 133 days.

This patent is subject to a terminal disclaimer.

(21) Appl. No.: 13/615,064

(22) Filed: Sep. 13, 2012

(65) Prior Publication Data

US 2013/0127721 A1    May 23, 2013

(30) Foreign Application Priority Data

Nov. 17, 2011   (TW) .............................. 100142000 A (51) Int. Cl.
*G09G 5/08* (2006.01)
*G06F 3/033* (2013.01)

(52) U.S. Cl.
CPC ..................................... *G06F 3/033* (2013.01)
USPC ........................................... 345/166; 345/163

(58) Field of Classification Search
USPC .......... 345/166–172; 600/322, 323, 300, 309, 600/310
See application file for complete search history.

(56) References Cited

U.S. PATENT DOCUMENTS

| 7,072,701 | B2 | 7/2006 | Chen et al. | |
|---|---|---|---|---|
| 2003/0036685 | A1* | 2/2003 | Goodman | 600/300 |
| 2005/0024335 | A1* | 2/2005 | Wang | 345/166 |
| 2009/0015558 | A1* | 1/2009 | Hung | 345/163 |
| 2009/0115727 | A1* | 5/2009 | Wu | 345/163 |
| 2009/0135140 | A1* | 5/2009 | Constantin et al. | 345/166 |
| 2009/0207137 | A1* | 8/2009 | Tan et al. | 345/166 |
| 2010/0066679 | A1* | 3/2010 | Pan | 345/166 |
| 2010/0123655 | A1* | 5/2010 | Lai | 345/156 |
| 2010/0207872 | A1* | 8/2010 | Chen et al. | 345/156 |

\* cited by examiner

*Primary Examiner* — Premal Patel
(74) *Attorney, Agent, or Firm* — Lowe Hauptman & Ham, LLP (57) ABSTRACT

There is provided a mouse control module including two light sources, an image sensor, a processing unit and a communication unit. The two light sources emit light of different wavelengths to illuminate a finger surface. The image sensor receives reflected light from the finger surface to generate a plurality of image frames. The processing unit detects a displacement of the finger surface and a physiological characteristic of a user according to the plurality of image frames. The communication unit encodes and/or sequences the displacement and the physiological characteristic so as to generate finger and physiology information. There is further provided an optical finger mouse.

18 Claims, 5 Drawing Sheets

OPTICAL FINGER MOUSE, MOUSE CONTROL MODULE AND PHYSIOLOGY DETECTION METHOD THEREOF

CROSS REFERENCE TO RELATED APPLICATION

This application claims the priority benefit of Taiwan Patent Application Serial Number 100142000, filed on Nov. 17, 2011, the full disclosure of which is incorporated herein by reference.

BACKGROUND

1. Field of the Disclosure

This disclosure generally relates to a human interface device and, more particularly, to a mouse control module and an optical finger mouse that may simultaneously detect a physiological characteristic of a user, a finger displacement and a finger contact status and output encoded, sequenced and/or compressed finger and physiology information.

2. Description of the Related Art

As the optical finger mouse has a relatively small size, it is suitable for being applied to portable electronic devices. An optical finger mouse can be used to detect an intensity variation of reflected light from a finger surface of a user so as to identify a finger contact status and a finger displacement with respect to a touch surface. However, with the development of industry, users spend more and more time on utilizing portable electronic devices that puts a lot of stress on their bodies. Therefore, if a portable electronic device also has the function of detecting physiological characteristics of a user and is able to give a warning when necessary, overuse of the portable electronic devices can then be avoided.

Conventional pulse oximeters utilize a noninvasive method to monitor the blood oxygenation and the heart rate of a user. A conventional pulse oximeter generally emits a red light beam (wavelength of about 660 nm) and an infrared light beam (wavelength of about 910 nm) to penetrate a part of the human body and detects an intensity variation of the penetrating light based on the feature that the oxyhemoglobin and the deoxyhemoglobin have different absorptivities in particular spectrum, e.g. referring to U.S. Pat. No. 7,072,701 and entitled "Method for spectrophotometric blood oxygenation monitoring". After the intensity variation of the penetrating light of the two wavelengths is detected, the blood oxygenation can be calculated according to equation (1):

$$\text{Oxygen saturation} = 100\% \times [HbO_2]/([HbO_2]+[Hb]) \quad (1)$$

wherein $[HbO_2]$ is an oxyhemoglobin concentration; and $[Hb]$ is a deoxy-hemoglobin concentration.

Figure 1:
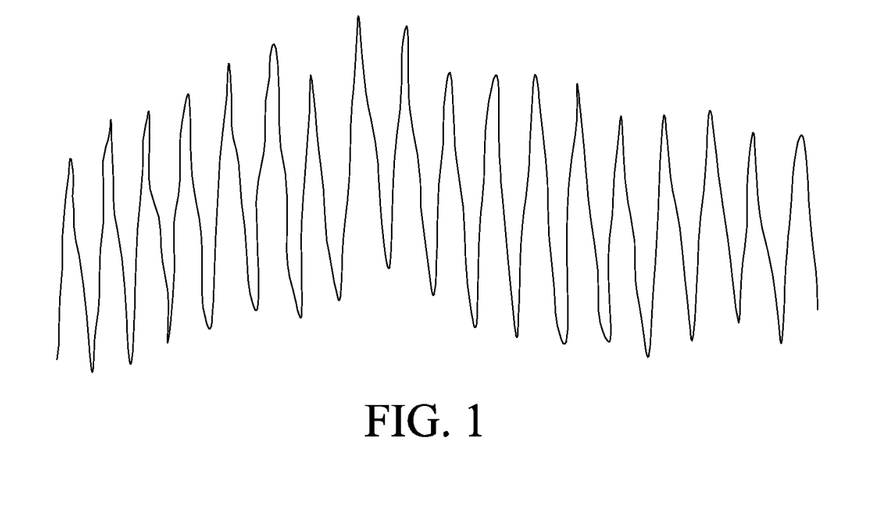
FIG. 1 shows a schematic diagram of an intensity variation of the penetrating light detected by pulse oximeters.

Generally, the intensity variation of the penetrating light of the two wavelengths detected by a pulse oximeter is similar to FIG. 1. This is because blood vessels will expand and contract with heartbeats such that the blood volume that the light beams pass through will change to accordingly change the ratio of light energy being absorbed. Therefore, the absorptivity of blood of different light spectra can be calculated according to the intensity information changing continuously so as to calculate the concentration information, e.g. the oxyhemoglobin and deoxyhemoglobin concentration, respectively. Finally, the blood oxygenation can be calculated according to equation (1).

However, as conventional pulse oximeters detect the intensity variation of the penetrating light, different intensity signals will be detected by detecting different parts of the human body. In addition, when the part of the human body being detected has a movement, a disturbed signal can be detected such that it is not possible to calculate correct physiological characteristics. Therefore, conventional pulse oximeters cannot be applied to portable electronic devices.

Accordingly, the present disclosure provides a mouse control module and an optical finger mouse that may simultaneously detect physiological characteristics of a user, a finger displacement and a finger contact status, and may output encoded, sequenced and/or compressed finger information and physiology information. The mouse control module and optical finger mouse of the present disclosure can eliminate the signal noise caused by the movement.

SUMMARY

It is an object of the present disclosure to provide a mouse control module and an optical finger mouse that may simultaneously calculate a finger displacement, a finger contact status and a physiological characteristic of a user by analyzing reflected light from a finger, and output encoded, sequenced and/or compressed finger and physiology information.

It is another object of the present disclosure to provide a mouse control module and an optical finger mouse that may simultaneously detect a finger displacement, a finger contact status and a physiological characteristic of a user, output encoded, sequenced and/or compressed finger and physiology information, and has a mechanism of eliminating the interference from ambient light sources.

It is another object of the present disclosure to provide a mouse control module and an optical finger mouse that may simultaneously detect a finger displacement, a finger contact status and a physiological characteristic of a user, output encoded, sequenced and/or compressed finger and physiology information, and has a denoising mechanism.

It is another object of the present disclosure to provide a mouse control module and an optical finger mouse that may simultaneously detect a finger displacement, a finger contact status and a physiological characteristic of a user, output encoded, sequenced and/or compressed finger and physiology information, and has a mechanism of regulating the system frequency.

It is another object of the present disclosure to provide a mouse control module and an optical finger mouse that may simultaneously detect a finger displacement, a finger contact status and a physiological characteristic of a user, output encoded, sequenced and/or compressed finger and physiology information, and enter a sleep mode after idling for a predetermined time period.

It is another object of the present disclosure to provide a mouse control module and an optical finger mouse that may simultaneously detect a finger displacement, a finger contact status and a physiological characteristic of a user, and output encoded, sequenced and/or compressed finger and physiology information, and the physiological characteristic may not be calculated or may be abandoned if the finger displacement is too large so as to prevent the mouse control module and optical finger mouse from outputting error physiology information.

The present disclosure provides a mouse control module configured to output finger information and physiology information of a finger. The mouse control module includes a first light source, a second light source, a light control unit, an image sensor, a processing unit and a communication unit. The first light source emits light of a first wavelength to the finger. The second light source emits light of a second wavelength to the finger. The light control unit is configured to control an on-state and an off-state of the first light source and the second light source. The image sensor is configured to capture reflected light from the finger at a sampling frequency to generate a plurality of first image frames corresponding to the on-state of the first light source and a plurality of second image frames corresponding to the on-state of the second light source. The processing unit is configured to calculate a displacement and a physiological characteristic according to the first image frames and the second image frames. The communication unit is configured to perform at least one of an encoding process and a sequential process on the displacement and the physiological characteristic to generate the finger information and the physiology information.

The present disclosure further provides an optical finger mouse includes a housing and a mouse chip. The housing includes a touch member touch-controlled by a finger. The mouse chip is disposed inside the housing and configured to simultaneously or alternatively provide light of different wavelengths to the finger, capture reflected light from the finger at a sampling frequency to generate a plurality of first image frames and second image frames respectively corresponding to on-states of the two different light sources, calculate a displacement and a physiological characteristic according to the first image frames and the second image frames, and perform at least one of an encoding process and a sequential process on the displacement and the physiological characteristic to generate finger information and physiology information.

The present disclosure further provides a physiology detection method of a mouse control module configured to output finger information and physiology information associated with a finger. The physiology detection method includes the steps of: providing light of a first wavelength and a second wavelength to the finger; capturing reflected light of the first wavelength to generate a plurality of first image frames and capturing reflected light of the second wavelength to generate a plurality of second image frames; dividing each of the first image frames and the second image frames into at least two parts and calculating an average brightness of each part; analyzing the average brightness of the each part of the first image frames to obtain a first intensity variation and analyzing the average brightness of the each part of the second image frames to obtain a second intensity variation; calculating a physiological characteristic according to the first intensity variation and the second intensity variation and calculating a displacement according to the first image frames and the second image frames; and performing at least one of an encoding process and a sequential process on the physiological characteristic and the displacement so as to output the finger information and the physiology information.

The mouse control module and optical finger mouse of the present disclosure may further compare a brightness value of the first image frames and the second image frames with a brightness threshold to identify a contact status.

In the mouse control module and the optical finger mouse of the present disclosure, the physiological characteristic includes a blood oxygenation and a heart rate. In the present disclosure, the movement informant and the physiology information are separated by means of independent component analysis (ICA) or blind source separation (BSS) so as to effectively eliminate the signal noise caused by the movement of the part of human body to be detected.

BRIEF DESCRIPTION OF THE DRAWINGS

Other objects, advantages, and novel features of the present disclosure will become more apparent from the following detailed description when taken in conjunction with the accompanying drawings.

DETAILED DESCRIPTION OF THE EMBODIMENT

It should be noted that, wherever possible, the same reference numbers will be used throughout the drawings to refer to the same or like parts.

Figure 2A:
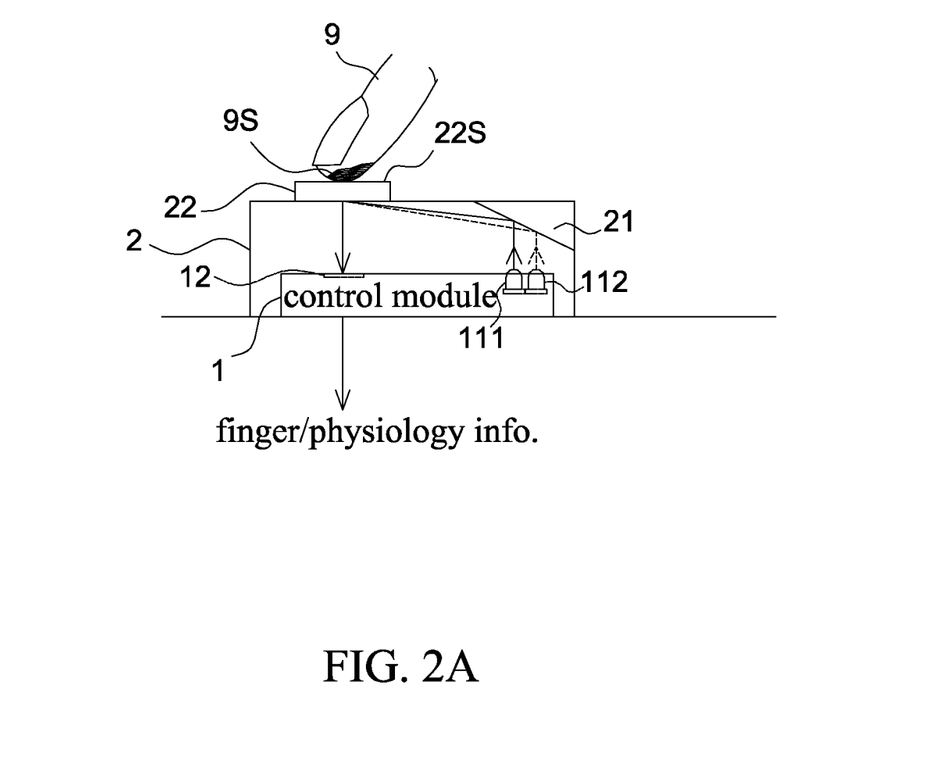
FIG. 2A shows a schematic diagram of the optical finger mouse according to an embodiment of the present disclosure.

Please refer to FIG. 2A, it shows a schematic diagram of the optical finger mouse according to an embodiment of the present disclosure. The optical finger mouse includes a mouse control module 1 and a housing 2, wherein the mouse control module 1 is disposed inside the housing 2 and the mouse control module 1 may be formed as a mouse chip or a package. It is appreciated that the position and the size of the mouse control module 1 in FIG. 2A are only exemplary and not used to limit the present disclosure. The mouse control module 1 is configured to detect and output encoded, sequenced and/or compressed finger information and physiology information, wherein the finger information may include a displacement and a contact status of a finger 9 of a user with respect to the optical finger mouse, and the physiology information may include a physiological characteristic of the user, such as a blood oxygenation and/or a heart rate. Generally, the optical finger mouse starts to calculate the displacement and the physiological characteristic when identifying that the contact status is a touch state (i.e. the finger 9 touches the optical finger mouse).

In FIG. 2A, the mouse control module 1 includes two light sources 111 and 112 and an image sensor 12, and the housing 2 includes a light guide 21 and a touch member 22, wherein the spatial relationship between every component is only exemplary and not used to limit the present disclosure. The two light sources 111 and 112 may be light emitting diodes or laser diodes and respectively emit light of different wavelengths. Preferably, said different wavelengths are the two wavelengths used in conventional pulse oximeters, e.g. red light of wavelength about 660 nm and infrared light of wavelength about 905, 910 or 940 nm. It is appreciated that the wavelengths mentioned herein are the center wavelength of corresponding illumination spectrum of the two light sources 111 and 112.

The light guide 21 is configured to direct the light emitted by the light sources 111 and 112 to the touch member 22. The light guide 22 is not limited to a reflecting surface, and it may allow the light emitted by the light sources 111 and 112 to penetrate through and transmit to the touch member 22. In other embodiments, if the light emitted from the light sources 111 and 112 can directly impinge on the touch member 22, the light guide 12 may not be implemented.

The touch member 22 has a touch surface 22S for the finger 9 to operate thereon, and the touch member 22 is preferably transparent to the light emitted by the light sources 111 and 112 such that when the finger 9 approaches or touches the touch surface 22S, the light emitted by the light sources 111 and 112 is reflected toward the interior of the housing 2. It is appreciated that an area of the touch surface 22S may be larger or smaller than that of the finger surface 9S.

The image sensor 12 receives, with a sampling parameter, reflected light from the touch member 22 (more specifically from the finger surface 9S) so as to generate a plurality of image frames, which may have a size of 16×16, wherein the sampling parameter may include an exposure time and an image gain, but not limited thereto. It is appreciated that FIG. 2A may further include a lens or lens set configured to guide the reflected light to the image sensor 12 so as to improve the sensing efficiency of the image sensor 12. The image sensor 12 is preferably an active matrix sensor, e.g. a CMOS image sensor, but it may also be other devices for detecting images.

The mouse control module 1 detects a displacement and a contact status of the finger 9 with respect to the touch surface 22S and a physiological characteristic of the user according to the image frames, and performs an encoding process, a sequential process and/or a compression process. The encoded, sequenced and/or compressed finger and physiology information may be sent, via a transmission interface, to an external device having a response device for displaying or corresponding control, wherein the response device may be a display device, a lamp device, a seven-segment display or a sound device. The external device may be a portable electronic device or a home appliance.

Figure 2B:
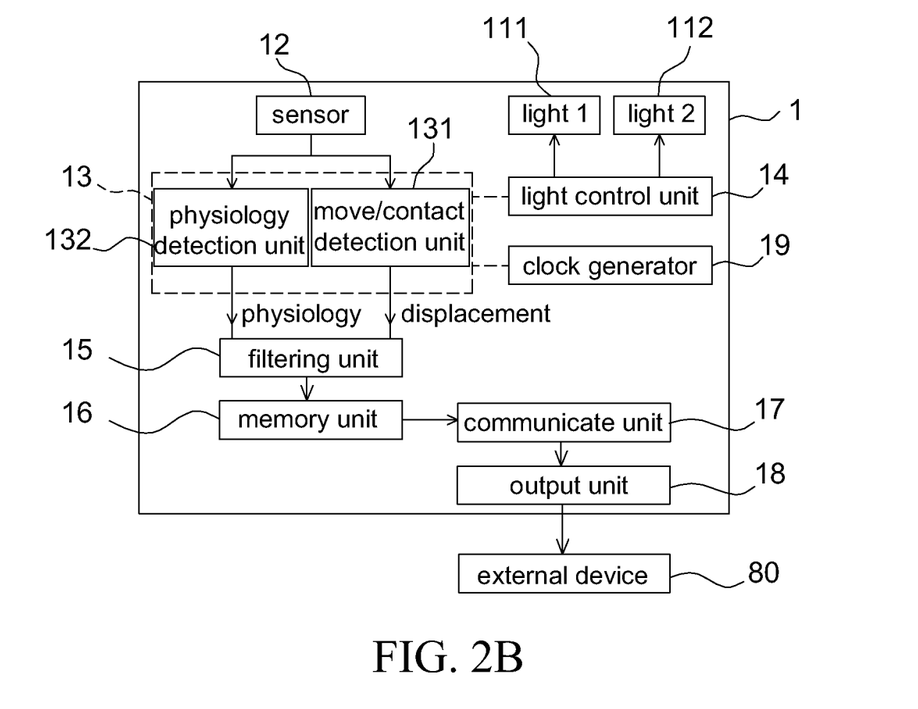
FIG. 2B shows a schematic block diagram of the mouse control module according to an embodiment of the present disclosure.

Please refer to FIGS. 2A and 2B, FIG. 2B shows a schematic block diagram of the mouse control module 1 according to the embodiment of the present disclosure. The mouse control module 1 includes a first light source 111, a second light source 112, the image sensor 12, a processing unit 13, a light control unit 14, a filtering unit 15, a memory unit 16, a communication unit 17, an output unit 18 and a clock generator 19, wherein because the processing unit 13 has multi-function, the processing unit 13 may further include a move/contact detection unit 131 configured to detect the displacement and contact status of the finger 9 with respect to the touch surface 22S and a physiology detection unit 132 configured to detect the physiological characteristic of the user. That is, the processing unit 13 may be a single element or composed of two elements.

The first light source 111 may emit red light of wavelength about 660 nm and the second light source 112 may emit infrared light of wavelength about 905, 910 or 940 nm Broadly speaking, the first light source 111 and the second light source 112 respectively emit light of the two wavelengths used in conventional pulse oximeters. The image sensor 12 receives reflected light from the finger 9 at a sampling frequency to generate a plurality of first image frames corresponding to on-states of the first light source 111 and a plurality of second image frames corresponding to on-states of the second light source 112. The processing unit 13 calculates a displacement, a contact status and a physiological characteristic according to the first image frames and the second image frames. The filtering unit 15 may be a lowpass filter and is configured to remove the noise in the data outputted from the processing unit 13. The light control unit 14 is coupled to the processing unit 13 and configured to control the ON/OFF (i.e. on-states and off-states) of the light sources 111 and 112 in correspondence with the image capturing of the image sensor 12. The memory unit 16 is configured to store the displacement, contact status, physiological characteristic obtained by the processing unit 13 and filtered by the filtering unit 15 and to store various parameters needed in the calculation. The communication unit 17 is configured to perform the encoding process, sequential process and/or compression process on the displacement, contact status and physiological characteristic stored in the memory unit 16 and to output finger information and physiology information. In other embodiments, said compression process may be performed by the output unit 18 or by a compression unit additionally disposed. The output unit 18 is configured to output the finger and physiology information to an external device 80. In addition, the optical finger mouse of the present disclosure preferably may further include a transmission interface unit configured to define the communication between the optical finger mouse and the external device 80. The external device 80 preferably includes at least one response device configured to display and/or respond the finger and physiology information received. The clock generator 19 is configured to provide the system frequency. In other embodiments, the filtering unit 15 may not be implemented.

The optical finger mouse of the present disclosure may incorporate with an external device 80 having a response device such that when a user controls a cursor shown on the response device or a software executed by the external device 80 through the optical finger mouse, the response device may simultaneously show the physiological characteristic of the user for reference. And when the physiological characteristic indicates that the user is in a fatigue state (e.g. according to a value of the physiological characteristic), the external device 80 may give a warning, wherein the method of showing the physiological characteristic and the warning may be implemented by, for example, showing on a screen, representing by a lamp device or by sound controlled by a software.

In other embodiments, the mouse control module 1 may include two image sensors configured to detect light of two different wavelengths respectively, wherein an optical bandpass filter may be integrated on one or two of the image sensors in order to select the desired spectrum.

Sampling Mechanism

The mouse control module 1 of the present disclosure includes two light sources and may perform two functions simultaneously, wherein the function of detecting the displacement and contact status may use the image frames associated with any wavelength without limitation, but the function of detecting the physiological characteristic needs to be performed corresponding to the image frames of respective wavelengths. First, the sampling mechanism of the image frames in the present disclosure is illustrated hereinafter.

Figure 3:
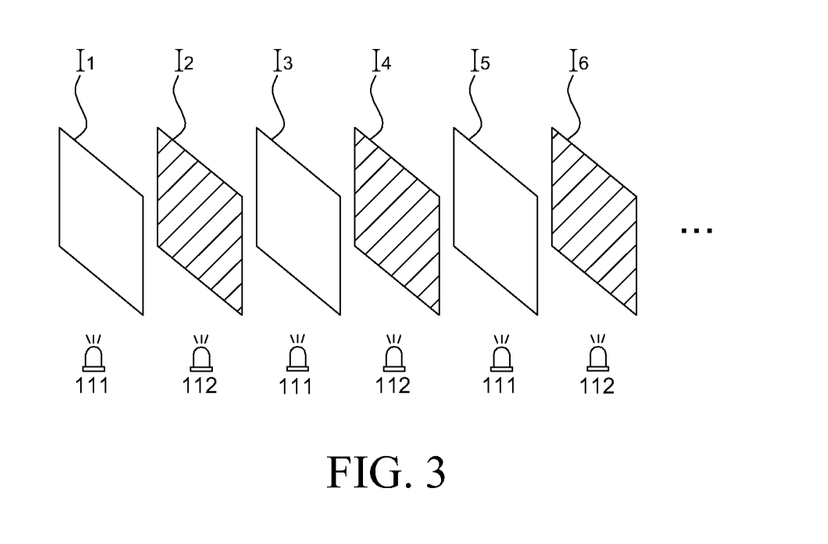
FIG. 3 shows a schematic diagram of the image frames captured by the image sensor of the mouse control module according to the embodiment of the present disclosure.

In one embodiment, the light control unit 14 controls the first light source 111 and the second light source 112 to turn on alternatively. The image sensor 12 captures image frames at a high and fixed sampling frequency (e.g. 3,000 frames/sec) and synchronizing to the turning on (i.e. on-states) of the first light source 111 or the second light source 112, and outputs a plurality of image frames $I_1$ to $I_6$... as shown in FIG. 3 to the processing unit 13 (or to the move/contact detection unit 131 and the physiology detection unit 132 simultaneously), wherein the image frames $I_1$ to $I_6$... include first image frames $I_1, I_3, I_5$... corresponding to the on-states of the first light source 111 and second image frames $I_2, I_4, I_6 \ldots$ corresponding to the on-states of the second light source 112.

The processing unit 13 (or the move/contact detection unit 131) may identify a contact status and calculate a displacement according to the first and second image frames $I_1$ to $I_6 \ldots$, e.g. identifying whether the finger 9 approaches or touches the touch surface 22S according to a comparison result of comparing a brightness value of the first and second image frames with at least one brightness threshold, wherein when the brightness value of the image frames is larger or smaller than the brightness threshold, a touch state is entered. After entering the touch state, the processing unit 13 may calculate the displacement according to the correlation between two first image frames, between one first image frame and one second image frame, or between two second image frames. It should be mentioned that although the method of identifying the contact status and calculating the displacement may use conventional methods, the identification process and the calculation process in the present disclosure need to use the image frames corresponding to the reflected light of two different wavelengths and thus are different from conventional navigation devices.

The processing unit 13 (or the physiology detection unit 132) may calculate an intensity variation of first image frame according to the first image frames $I_1, I_3, I_5 \ldots$, and calculates an intensity variation of second image frame according to the second image frames $I_2, I_4, I_6 \ldots$ (described later), and accordingly calculate the absorptivity of blood at two different spectra so as to obtain [HbO$_2$] and [Hb]. Finally, the blood oxygenation may be calculated according to equation (1), and the heart rate may also be calculated according to a comparison result of comparing the intensity variation of first image frame and/or the intensity variation of second image frame with at least one pulse threshold.

Figure 4:
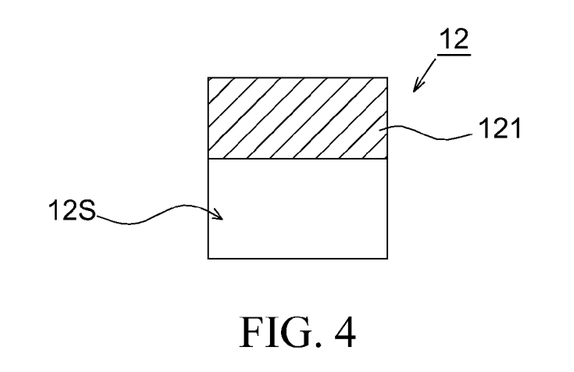
FIG. 4 shows a schematic diagram of the image sensor of the mouse control module according to the embodiment of the present disclosure, wherein an optical filter is disposed in front of a part of a sensing surface of the image sensor.

In another embodiment, the light control unit 14 controls the first light source 111 and the second light source 112 to turn on simultaneously and synchronizing to the image capturing of the image sensor 12; that is, the image sensor 12 may receive reflected light of two wavelengths simultaneously. Therefore, in this embodiment an optical filter 121 is further disposed in front of at least a part of a sensing surface 12S of the image sensor 12 as shown in FIG. 4, wherein the optical filter 121 may be an optical bandpass filter to allow the part of the sensing surface 12S behind the optical filter 121 to only receive the spectrum of light of the first light source 111 or the second light source 112 such that the processing unit 13 (or the move/contact detection unit 131 and the physiology detection unit 132) may distinguish the first image frame (i.e. the part of the image frame associated with the first light source 111) and the second image frame (i.e. the part of the image frame associated with the second light source 112). It is appreciated that in the present disclosure the position and the area of the optical filter 121 are not limited to those shown in FIG. 4.

In this manner, the processing unit 13 (or the move/contact detection unit 131) may also calculate a contact status and a displacement according to the first image frames and the second image frames $I_1$ to $I_6 \ldots$. The processing unit 13 (or the physiology detection unit 132) may also calculate the intensity variation of first image frame according to the first image frames $I_1, I_3, I_5 \ldots$, calculate the intensity variation of second image frame according to the second image frames $I_2, I_4, I_6 \ldots$, and calculate the blood oxygenation and the heart rate according to the two intensity variations.

It is appreciated that as the sensing efficiency of the image sensor 12 toward light of different wavelengths may be different or the illumination brightness values of the first light source 111 and the second light source 112 may not be exactly identical, the brightness value of the image frames captured by the image sensor 12 may be previously adjusted (e.g. by adjusting the sampling parameter, such as an exposure time and an image gain, of the image frames corresponding to different wavelengths) before shipment such that the image frames initially outputted by the image sensor 12 may have substantially identical brightness values so as to improve the identification accuracy.

In this embodiment, the mouse control module 1 simultaneously or alternatively provides light of different wavelengths to the finger 9, captures reflected light from the finger 9 at a sampling frequency to generate a plurality of first image frames and second image frames corresponding to on-states of the two light sources, and calculates the contact status, displacement and physiological characteristic according to the first image frames and the second image frames. The mouse control module 1 further performs an encoding process, a sequential process and/or a compression process on the displacement and/or physiological characteristic so as to output finger information (i.e. processed displacement) and physiology information (i.e. processed physiological characteristic).

Mechanism of Eliminating Ambient Light Interference

In FIG. 2A, as the touch member 22 and the finger 9 are light transmissive, the ambient light outside the optical finger mouse can penetrate the finger 9 and the touch member 22 and then be received by the image sensor 12 to degrade the image quality of the image frames captured thereby. In the present disclosure, the light control unit 14 may control the first light source 111 and the second light source 112 to turn off (i.e. the off-state) in predetermined time intervals.

Figure 5:
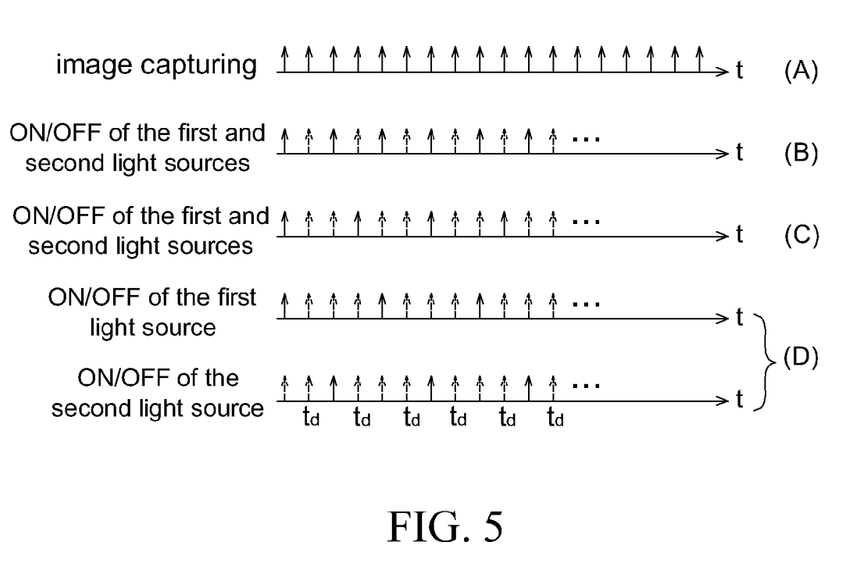
FIG. 5 shows a schematic diagram of the image capturing of the image sensor and the ON/OFF of the light source in the mouse control module according to the embodiment of the present disclosure.

For example please refer to FIG. 5, it shows a schematic diagram of the image capturing of the image sensor 12 and the ON/OFF of the first light source 111 and the second light source 112, wherein in FIGS. 5(B)-5(D) solid arrows denote the on-states of the light sources and dashed arrows denote the off-states of the light sources. FIG. 5(A) shows that the image sensor 12 captures image frames at a fixed sampling frequency. FIG. 5(B) shows that the first light source 111 and the second light source 112 are alternatively turned on and turned off at the same time, and thus the image sensor 12 may alternatively capture bright image frames (i.e. corresponding to the on-states of the light sources) and dark image frames (i.e. corresponding to the off-states of the light sources). FIG. 5(C) shows that the first light source 111 and the second light source 112 are simultaneously turned on once after turning off two image periods, and this embodiment is generally for a lower displacement of the finger 9 compared to FIG. 5(B). As mentioned above, when the first light source 111 and the second light source 112 are turned on simultaneously (FIGS. 5(B) and 5(C)), the image sensor 12 further includes an optical filter 121 (as shown in FIG. 4) for spatially distinguishing the image frame associated with different light sources such that one part of the image sensor 12 may sense reflected light associated with the first light source 111 and the other part thereof may sense reflected light associated with the second light source 112.

When the finger 9 touches or approaches the touch surface 22S, the bright image frames, which are associated with the on-states of the light sources, include components of (reflected light from finger+stray light+ambient light), and the dark image frames, which are associated with the off-states of the light sources, include only the component of (ambient light). Therefore, if a dark image frame is subtracted from a bright image frame, the interference from the ambient light can be effectively eliminated. The processing unit 13 may calculate the displacement, contact status and physiological characteristic according to differential images between the bright image frames and the dark image frames.

Please refer to FIG. 5(D), it shows an embodiment in which the first light source 111 and the second light source 112 are turned on alternatively. In this embodiment, in order to allow the image sensor 12 to be able to capture dark image frames, the light control unit 14 controls the first light source 111 and the second light source 112 to alternatively turn on every other image frame, e.g. the two light sources are both turned off at time $t_d$ in FIG. 5(D). Accordingly, the processing unit 13 may calculate a differential first image (i.e. bright first image frame—dark image frame) and a differential second image (i.e. bright second image frame—dark image frame), and calculate the displacement, contact status and physiological characteristic according to the differential first and second images. As mentioned above, if the first light source 111 and the second light source 112 are turned on alternatively, the mouse control module 1 temporally distinguishes the image frames associated with different light sources.

In this embodiment, the light control unit 14 controls the first light source 111 and the second light source 112 to turn on simultaneously or alternatively and the image sensor 12 is able to capture dark image frames when both the light sources are turned off. The interference from ambient light is eliminated by calculating a difference between bright and dark image frames. It is appreciated that the on-states and off-states of each light source shown in FIG. 5 are only exemplary and are not used to limit the present disclosure.

Denoising Mechanism

As the image frames captured by the image sensor 12 generally include noise which is randomly distributed in the image frames being captured. Therefore, in the present disclosure it is able to calculate a sum of M image frames to increase the signal-to-noise ratio (SNR) thereby improving the calculation accuracy of the physiological characteristic. For example, it is able to calculate a sum of 10 image frames and every group of 10 image frames may have partially repeated image frames or totally different 10 image frames. It is appreciated that if the first light source 111 and the second light source 112 are turned on alternatively, the sum of M image frames in this embodiment may be a sum of M first image frames (e.g. $I_1+I_3+I_5+$ ... as shown in FIG. 3) and a sum of M second image frames (e.g. $I_2+I_4+I_6+$ ... as shown in FIG. 3) since two intensity variations need to be calculated respectively. However, if the first light source 111 and the second light source 112 are turned on simultaneously, the sum of M image frames in this embodiment is a sum of M successive image frames (e.g. $I_1+I_2+I_3+I_4+I_5+I_6+$ ... as shown in FIG. 3), and the two intensity variations may be distinguished by post-processing to accomplish spatially distinguishing. In addition, if the mechanism of eliminating ambient light interference described above is incorporated in this embodiment, the sum of M image frames of this embodiment is a sum of M differential images; that is, the process of eliminating ambient light interference is performed and then the process of denoising is performed successively. In other embodiments, only one of the mechanism of eliminating ambient light interference and the denoising mechanism is performed.

As mentioned above, the image sensor 12 may capture image frames with different sampling parameters, e.g. the image sensor 12 may have different absorptions of light at different wavelengths, and thus different sampling parameters, such as different exposure times and different image gains, may be used to make the first image frame and the second image frame have substantially identical initial brightness values in order to correctly perform the post-processing on the image frames; that is, the sampling parameters associated with the first image frames and the second image frames may be different. In the present disclosure, in order to eliminate the influence of different sampling parameters, every image frame or a sum of M image frames or an average of M image frames may be normalized by the sampling parameter, e.g. (a sum of M image frames/sampling parameter) or (an average of M image frames/sampling parameter), wherein M is a positive integer.

Calculating Physiological Characteristics

Corresponding to the on-states of different light sources, the image frames captured by the image sensor 12 may contain physiology information and movement information at the same time. Therefore, in the present disclosure the processing unit 13 (or the physiology detection unit 132) has to separate two types of information at first and then is able to calculate the physiological characteristic correctly. In the present disclosure, the processing unit 13 may separate the two types of information according to, for example, independent component analysis (ICA) or blind source separation (BSS).

Figure 6:
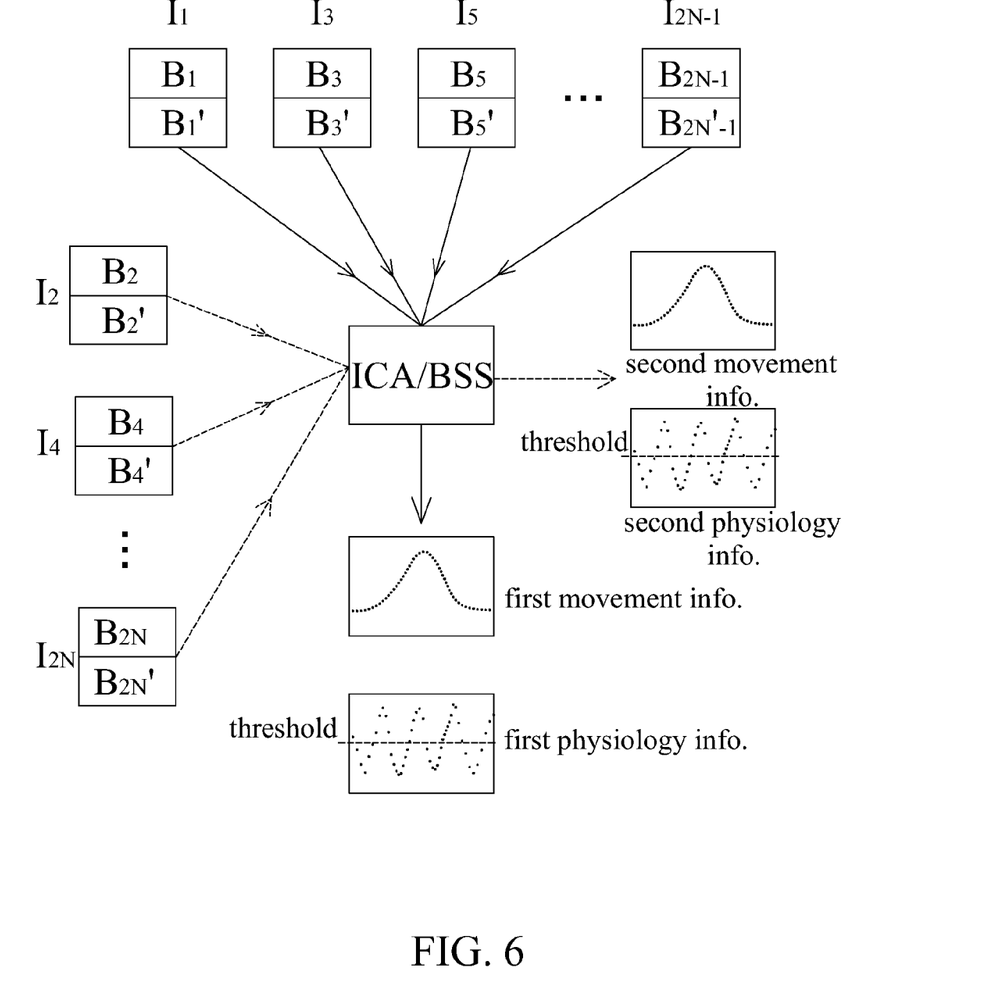
FIG. 6 shows a schematic diagram of separating the movement information and the physiology information by the processing unit of the mouse control module according to the embodiment of the present disclosure.

Please refer to FIGS. 3 and 6, first taking the first image frames $I_1, I_3, I_5$ ... shown in FIG. 3 as an example, each of the first image frames (e.g. original first image frames or the first image frames processed by the mechanism of eliminating ambient light interference and/or normalizing mechanism) or each of the sum of a plurality of first image frames (e.g. a sum of M original first image frames or a sum of M first image frames processed by the mechanism of eliminating ambient light interference and/or normalizing mechanism) is divided into at least two parts and an average brightness of each part is calculated, e.g. the image frame $I_1$ is divided into an upper and a lower part respectively having an average brightness $B_{2N-1}$ and $B_{2N-1}'$; the image frame $I_3$ is divided into an upper and a lower part respectively having an average brightness $B_3$ and $B_3'$; ... ; the image frame $I_{2N-1}$ is divided into an upper and a lower part respectively having an average brightness $B_{2N-1}$ and $B_{2N-1}'$, wherein the image frames may be divided into more than two parts in other embodiments. Next, a first movement informant and a first physiology information is separated from the divided image frames according to independent component analysis (ICA) or blind source separation (BSS) method as shown in FIG. 6, and each of the information is shown as a curve of intensity variation. In the present disclosure the movement information is abandoned and the physiological characteristic is calculated only according to the physiology information. It is appreciated that as the sampling frequency of the image sensor 12 is much higher than the heart rate, the separated physiology information is shown as a curve of the intensity variation in accordance with the pulse beating (i.e. similar to FIG. 1), but the separated movement information is not limited to that shown in FIG. 6. In addition, the two parts divided from the image frames are not necessary to be the upper and lower parts of the image frames. In addition, as it is necessary to respectively calculate the physiology information associated with two wavelengths, the aforementioned separation process is performed respectively on the first image frames $I_1, I_3, I_5$ ... (i.e. corresponding to the on-state of the first light source) and the second image frames $I_2, I_4, I_6$ ... (i.e. corresponding to the on-state of the second light source) such that second movement information and second physiology information can also be retrieved from the second image frames $I_2, I_4, I_6$ .... It should be mentioned that, if the information separation is performed on the sum or average of the image frames, each of $I_1$ to $I_{2N-1}$ and $I_2$ to $I_{2N}$ shown in FIG. 6 represents a sum or an average of M image frames.

It should be mentioned that the displacement and the contact status of the finger 9 are calculated by the processing unit 13 (or the move/contact detection unit 131) directly according to the original first image frames and second image frames without using the separated movement information. The ICA and BSS methods are mainly configured to separate combined signals. When the separated movement information is abandoned, it is able to eliminate the signal noise caused by the movement.

In the present disclosure, the processing unit 13 further calculates a heart rate according to a comparison result of comparing at least one pulse threshold with a first intensity variation (i.e. the first physiology information) and/or a second intensity variation (i.e. the second physiology information).

Mechanism of Regulating System Frequency

In order to reduce the system cost, the clock generator 19 may use a RC oscillator circuit. Although the RC oscillator circuit has a lower cost, it also has a lower precision as its oscillating frequency can change with the manufacturing process and operating temperature. The crystal oscillator may also be utilized in other embodiments. In calculating physiological characteristics, a precise system frequency is necessary (e.g. in calculating the heart rate). Therefore, preferably a reference to regulate the oscillating frequency of the clock generator 19 of the mouse control module 1 may be constructed before shipment; for example, an external light source having a precise lighting frequency may be attached to the touch surface 22S of the touch member 22 to allow the image sensor 12 to detect the intensity variation of the external light source; then, a difference between the oscillating frequency of the clock generator 19 under different operating temperatures and the precise lighting frequency may be recorded previously to be served as a system frequency calibration parameter and pre-stored in the memory unit 16. And the system frequency can be precisely adjusted based on the system frequency calibration parameter when necessary.

Sleep Mode

The mouse control module 1 of the present disclosure may enter a sleep mode after idling for a predetermined time period. For example, when the processing unit 13 identifies that a finger 9 does not approach or touch the touch surface 22S within the predetermined time period, the sleep mode is entered.

Mechanism of Removing Physiological Characteristic

Although the processing unit 13 of the mouse control module 1 of the present disclosure may calculate the displacement and the physiological characteristic simultaneously, accurate physiological characteristics can only be obtained when the displacement is relatively small. Therefore, in the present disclosure the processing unit 13 may previously identify whether the displacement is larger than a predetermined value (i.e. a displacement threshold). When the displacement is larger than the predetermined value, the image frames captured by the image sensor 12 are only used to calculate the displacement or to identify the contact status but not used to calculate the physiological characteristic; or even though the physiological characteristic is calculated, the physiological characteristic is directly removed from the memory unit 16. The predetermined value may be determined according to different applications, e.g. according the size of the sensing surface 12S and/or the searching block.

Figure 7:
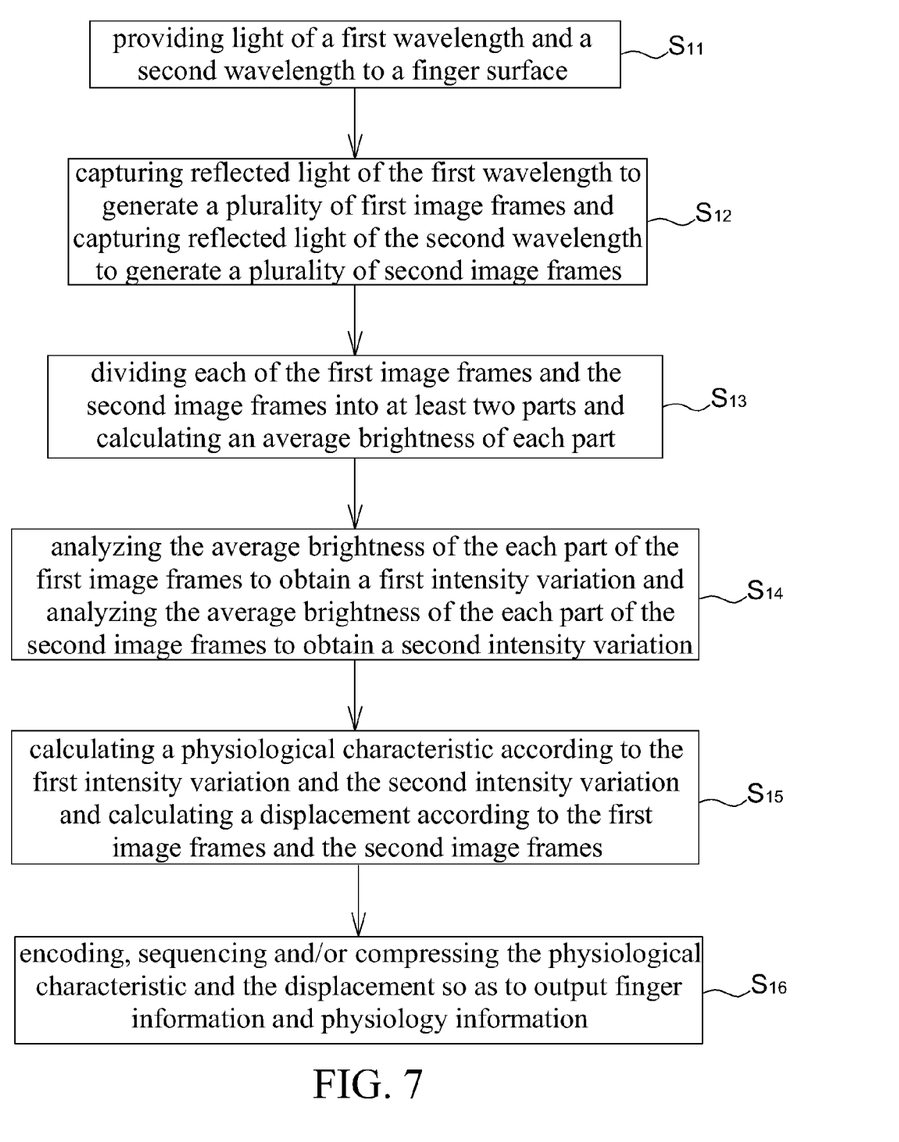
FIG. 7 shows a flow chart of the physiology detection method according to the embodiment of the present disclosure.

The mouse control module 1 of the present disclosure detects and outputs finger information and physiology information associated with a finger according to the physiology detection method below, which includes the steps of: providing light of a first wavelength and a second wavelength to a finger surface (Step $S_{11}$); capturing reflected light of the first wavelength to generate a plurality of first image frames and capturing reflected light of the second wavelength to generate a plurality of second image frames (Step $S_{12}$); dividing each of the first image frames and the second image frames into at least two parts and calculating an average brightness of each part (Step $S_{13}$); using independent component analysis or blind source separation to analyze the average brightness of the each part of the first image frames to obtain a first intensity variation and to analyze the average brightness of the each part of the second image frames to obtain a second intensity variation (Step $S_{14}$); and calculating a physiological characteristic according to the first intensity variation and the second intensity variation and calculating a displacement according to the first image frames and the second image frames (Step $S_{15}$); performing at least one of an encoding process, a sequential process and a compression process on the physiological characteristic and the displacement so as to output the finger information and the physiology information (Step $S_{16}$).

The physiology detection method of the present disclosure may calculate a physiological characteristic through detecting the skin surface of a part of the human body. Therefore, the detection function may be executed only by replacing the finger 9 used in aforementioned embodiments by another part of the human body. The physiology detection method of the present disclosure further includes the mechanisms of denoising, eliminating ambient light interference, entering sleep mode and regulating system frequency. Said another part of the human body may be the part of human body to be detected in conventional pulse oximeters.

As mentioned above, the conventional optical finger mouse can not detect the physiological characteristic of a user and the method of calculating the blood oxygenation for pulse oximeters cannot be applied to an optical finger mouse since it can not detect a moving object. Therefore, the present disclosure further provides an optical finger mouse (FIG. 2A) and a mouse control module (FIG. 2B) that can detect the finger displacement and the physiological characteristic of a user simultaneously, and output encoded, sequenced and/or compressed finger and physiology information. The optical finger mouse and mouse control module of the present disclosure can effectively eliminate the signal noise caused by movement and the interference from ambient light source, and further has the mechanisms of regulating the system frequency, entering sleep mode and removing invalid physiology information.

Although the disclosure has been explained in relation to its preferred embodiment, it is not used to limit the disclosure. It is to be understood that many other possible modifications and variations can be made by those skilled in the art without departing from the spirit and scope of the disclosure as hereinafter claimed.

What is claimed is:

1. A mouse control module configured to output finger information and physiology information of a finger, the mouse control module comprising:

a first light source configured to emit light of a first wavelength to the finger;

a second light source configured to emit light of a second wavelength to the finger;

a light control unit configured to control an on-state and an off-state of the first light source and the second light source;

an image sensor configured to capture reflected light from the finger at a sampling frequency to generate a plurality of first image frames corresponding to the on-state of the first light source and a plurality of second image frames corresponding to the on-state of the second light source;

a processing unit configured to
calculate a displacement according to the first image frames and the second image frames,
divide each of the first image frames into at least two parts and calculate an average brightness of each part,
analyze the average brightness of the each part of the first image frames to obtain a first intensity variation,
divide each of the second image frames into at least two parts and calculate an average brightness of each part,
analyze the average brightness of the each part of the second image frames to obtain a second intensity variation, and
calculate a physiological characteristic according to the first intensity variation and the second intensity variation; and a communication unit configured to perform at least one of an encoding process and a sequential process on the displacement and the physiological characteristic to generate the finger information and the physiology information.

2. The mouse control module as claimed in claim 1, wherein the mouse control module is a mouse chip or a package.

3. The mouse control module as claimed in claim 1, wherein the processing unit is further configured to calculate a heart rate according to a comparison result of comparing at least one pulse threshold with at least one of the first intensity variation and the second intensity variation.

4. The mouse control module as claimed in claim 1, wherein the physiological characteristic comprises a blood oxygenation and a heart rate.

5. The mouse control module as claimed in claim 1, wherein the processing unit further calculates a sum of M image frames, and normalizes the sum or an average of the M image frames with a sampling parameter, wherein M is a positive integer.

6. The mouse control module as claimed in claim 1, wherein
the light control unit is configured to enable the off-state of the first light source and the second light source for predetermined time intervals such that the image sensor captures a plurality of bright first image frames, a plurality of bright second image frames and a plurality of dark image frames; and
the processing unit is configured to calculate the displacement and the physiological characteristic according to a difference between the bright first image frames and the dark image frames and according to a difference between the bright second image frames and the dark image frames.

7. The mouse control module as claimed in claim 1, wherein the mouse control module is configured to enter a sleep mode after idling for a predetermined time period.

8. The mouse control module as claimed in claim 1, wherein the processing unit is configured to not calculate the physiological characteristic or abandon the physiological characteristic when the displacement is larger than a predetermined value.

9. The mouse control module as claimed in claim 1, further comprising a memory unit configured to store a system frequency calibration parameter, the displacement and the physiological characteristic.

10. The mouse control module as claimed in claim 1, wherein the processing unit is further configured to compare a brightness value of the first image frames and the second image frames with a brightness threshold to identify a contact status.

11. The mouse control module as claimed in claim 1, wherein the processing unit is configured to calculate the displacement according to two of the first image frames, one of the first image frames and one of the second image frames, and two of the second image frames.

12. The mouse control module as claimed in claim 1, wherein
the light control unit is configured to alternatively enable the on-state of the first light source and the second light source such that the image sensor receives the reflected light associated with the first light source and the second light source alternatively; or
the light control unit is configured to simultaneously enable the on-state of the first light source and the second light source such that the image sensor receives the reflected light associated with the first light source and the second light source simultaneously, and the image sensor comprises an optical filter covering at least a part of a sensing surface thereof.

13. The mouse control module as claimed in claim 1, further comprising an output unit configured to output the displacement and the physiological characteristic or output compressed displacement and compressed physiological characteristic.

14. An optical finger mouse, comprising:
a housing comprising a touch member touch-controlled by a finger; and
a mouse chip disposed inside the housing and configured to
simultaneously or alternatively provide light of different wavelengths to the finger,
capture reflected light from the finger at a sampling frequency to generate a plurality of first image frames and second image frames respectively corresponding to on-states of the two different light sources,
calculate a displacement according to the first image frames and the second image frames,
divide each of the first image frames into at least two parts and calculate an average brightness of each part,
analyze the average brightness of the each part of the first image frames to obtain a first intensity variation,
divide each of the second image frames into at least two parts and calculate an average brightness of each part,
analyze the average brightness of the each part of the second image frames to obtain a second intensity variation,
calculate a physiological characteristic according to the first intensity variation and the second intensity variation, and
perform at least one of an encoding process and a sequential process on the displacement and the physiological characteristic to generate finger information and physiology information.

15. The optical finger mouse as claimed in claim 14, wherein the physiological characteristic comprises a blood oxygenation and a heart rate.

16. The optical finger mouse as claimed in claim 14, wherein the mouse chip is further configured to calculate a heart rate according to a comparison result of comparing at least one pulse threshold with at least one of the first intensity variation and the second intensity variation.

17. The optical finger mouse as claimed in claim 14, wherein the mouse chip is further configured to compare a brightness value of the first image frames and the second image frames with a brightness threshold to identify a contact status.

18. A physiology detection method of a mouse control module configured to output finger information and physiology information associated with a finger, the physiology detection method comprising:
- providing light of a first wavelength and a second wavelength to the finger;
- capturing reflected light of the first wavelength to generate a plurality of first image frames and capturing reflected light of the second wavelength to generate a plurality of second image frames;
- dividing each of the first image frames and the second image frames into at least two parts and calculating an average brightness of each part;
- analyzing the average brightness of the each part of the first image frames to obtain a first intensity variation and analyzing the average brightness of the each part of the second image frames to obtain a second intensity variation;
- calculating a physiological characteristic according to the first intensity variation and the second intensity variation and calculating a displacement according to the first image frames and the second image frames; and
- performing at least one of an encoding process and a sequential process on the physiological characteristic and the displacement so as to output the finger information and the physiology information.

\* \* \* \* \*